(12) United States Patent
Maillefer et al.

(10) Patent No.: US 7,854,234 B2
(45) Date of Patent: Dec. 21, 2010

(54) METHOD OF SETTING UP, CARING FOR AND LATER REMOVING A TEMPORARY RASTA HAIRSTYLE

(75) Inventors: Sarah Maillefer, Middes (CH); Axel Kalbfleisch, Darmstadt (DE); Andre Rehmann, Schmitten (CH); Daniel Chambettaz, Ursen (CH)

(73) Assignee: Wella AG, Darmstadt (DE)

( * ) Notice: Subject to any disclaimer, the term of this patent is extended or adjusted under 35 U.S.C. 154(b) by 625 days.

(21) Appl. No.: 11/490,293

(22) Filed: Jul. 20, 2006

(65) Prior Publication Data

US 2006/0257345 A1 Nov. 16, 2006

Related U.S. Application Data

(60) Division of application No. 10/443,707, filed on May 22, 2003, now abandoned, which is a continuation-in-part of application No. 10/309,468, filed on Dec. 4, 2002, now abandoned.

(30) Foreign Application Priority Data

Jul. 31, 2002 (DE) ................ 102 34 804

(51) Int. Cl.
*A61K 8/18* (2006.01)
*A45D 7/00* (2006.01)

(52) U.S. Cl. .................... 132/202; 132/200
(58) Field of Classification Search ........... 132/202, 132/203, 209, 200; 424/47, 70.11
See application file for complete search history.

(56) References Cited

U.S. PATENT DOCUMENTS

| | | | | |
|---|---|---|---|---|
| 1,660,729 | A * | 2/1928 | Strock | 15/244.4 |
| 3,333,292 | A * | 8/1967 | Chase et al. | 401/123 |
| 4,058,131 | A * | 11/1977 | Crawford et al. | 132/203 |
| 5,307,825 | A | 5/1994 | Smith | |
| 5,415,856 | A * | 5/1995 | Crews et al. | 424/70.2 |
| 5,587,174 | A | 12/1996 | Lang et al. | |
| 5,679,327 | A * | 10/1997 | Darkwa et al. | 424/70.4 |
| 6,039,960 | A * | 3/2000 | Chung et al. | 424/401 |
| 6,520,186 | B2 * | 2/2003 | Rollat et al. | 132/203 |
| 6,524,563 | B1 * | 2/2003 | Wire et al. | 424/70.12 |
| 6,582,679 | B2 | 6/2003 | Stein et al. | |
| 2002/0122811 | A1 | 9/2002 | Stein | |
| 2002/0164298 | A1 * | 11/2002 | Birkel et al. | 424/70.11 |
| 2002/0189629 | A1 * | 12/2002 | McGriff, III | 132/227 |
| 2003/0131868 | A1 * | 7/2003 | Stanley, III | 132/294 |
| 2003/0202953 | A1 * | 10/2003 | Tamareselvy et al. | 424/70.16 |
| 2003/0211070 | A1 | 11/2003 | Stein | |
| 2005/0074413 | A1 * | 4/2005 | Belli et al. | 424/47 |

FOREIGN PATENT DOCUMENTS

| | | |
|---|---|---|
| DE | 25 42 338 | 3/1977 |
| DE | 100 49 147 A1 | 4/2002 |
| FR | 1 075 047 | 10/1954 |
| JP | S45-26873 | 9/1970 |
| JP | 05/238922 | 9/1993 |
| JP | 10-033241 | 2/1998 |
| JP | 2001-316 228 | 11/2001 |
| WO | 97/38667 | 10/1997 |

OTHER PUBLICATIONS

Dreadlocks www.howtodread.com/dreadlocks.html Oct. 17, 2002.*
WO 99/00105 "Hair Styling Compostion" Schofield Jan. 7, 1999.*
Paul: "Backcombed Dreadlock" Internet Articles Online, Aug. 13, 2001, XP002263623.
FBB Inc: "Take Down" Internet Article, 'Online! Jun. 2, 2002, XP002263627.
Karen M. Shelton: "Dreadlocks: A Sizzling Hot Hair Trend . . ." Hairboutique Articles, 'Online! Dec. 28, 2001, XP002263626.
Smoore et al: "Making Locks . . ." Internet Article, 'Online!, Mar. 1, 2002, XP 002263624.
Salon Collective: "Knotty Boy Dread Stuff" Internet Article, 'Online!, Jun. 5, 2002, XP002263625.
Ullmanns' Encyclopedia of Industrial Chemistry, 4th Edition, Vloume 24, p. 3.

* cited by examiner

*Primary Examiner*—Rachel R Steitz
(74) *Attorney, Agent, or Firm*—Michael J. Striker

(57) ABSTRACT

A method of setting up, caring for and later removing a temporary rasta hairstyle is described. This method includes one or more of the following steps: applying a roughness-increasing substance to the hair to roughen the hair, applying an adherence-increasing substance to the hair to increase adherence of hairs to each other, and subsequently setting up the temporary rasta hairstyle by intertwining hair strandwise. The cleaning of the temporary rasta hairstyle occurs preferably using a concave sponge, without disturbing the temporary rasta hairstyle. To again remove the temporary rasta hairstyle a composition that increases the combability is applied to the hair and the rasta strands are opened and unwound or untwisted. Multi-component kits and compositions for performing the method are also described.

10 Claims, No Drawings

METHOD OF SETTING UP, CARING FOR AND LATER REMOVING A TEMPORARY RASTA HAIRSTYLE

CROSS-REFERENCE

This is a divisional of U.S. patent application, Ser. No. 10/443,707, filed on May 22, 2003 now abandoned, which, in turn, is a continuation-in-part of U.S. patent application, Ser. No. 10/309,468, filed on Dec. 4, 2002 now abandoned. This divisional application claims the benefit of priority under 35 U.S.C. 120 based on U.S. patent application, Ser. No. 10/443,707.

BACKGROUND OF THE INVENTION

1. Field of the Invention

The present invention relates to methods for setting up, caring for and later removing a temporary rasta hairstyle, to compositions and, ingredients used in the methods and to multi-part kits for performing the methods.

2. Description of the Related Art

A permanent rasta hairstyle is a hair fashion comprising tightly braided long braids usually comprising thin and extremely strongly interlocked hair strands. These types of hairstyles are also called dreadlocks. Both names are used synonymously in the following description. Ethnic hair (e.g. African or Afro-American hair, so-called kinky hair) is ideal for setting up dreadlocks or rasta hairstyles because of its naturally curliness and its nature. However rasta hairstyles can be set up with other, among others, smooth, hair, such as middle European or Asiatic hair, with suitable techniques. It is necessary however to produce a hair structure that tends to facilitate strongly interlocking the hair strands prior to forming the locks. This usually occurs by a combination of chemical and mechanical treatments of the hair. First it is necessary that the hair is made dull. Hair flake or scale should not be present on the hair shaft, but should be removed as much as possible. The chemical treatment can occur with a hair reducing agent (e.g. thio compounds, such as thioglycolic acid), such as is used in a permanent wave treatment, but with the difference that the effective concentration and/or action is greatly increased. During this latter treatment the cuticle layer is probably at least partially or entirely removed to increase the required tendency of the hair strands to interlock. Another chemical treatment is an alkaline treatment with strong alkali compositions, e.g. corn soap or an alkaline shampoo without care additives. Furthermore an intense mechanical treatment of the hair is required to remove the flake or scale. This can occur by an intense "toupier" of the hair as strong as possible for several hours with a very fine comb, e.g. with a lice comb or similar comb, usually with stable metal teeth. "Toupier" of the hair is also called "back-combing". These terms are used synonymously in the following. During back-combing there is an intense irreversible interlocking of the hair and the hair is irreparably damaged. Another problem besides hair damage is that the rasta hair style is permanent when set up with the conventional hair techniques and is not removable. The interlocking of the hair is irreversible, i.e. it cannot be reversed without damaging the user's hair. Those who set up this hairstyle once only remove it by cutting off the hair with scissors. Some fashion-conscious users would like to have a rasta hairstyle only temporarily or only for a certain occasion, e.g. for a party on the weekend, and would like to switch back to their original hairstyle the next day without damaging their hair. Thus there is a strong demand for a removable temporary rasta hairstyle that does not entail damaging hair treatment steps. An additional problem with the conventionally set up rasta hairstyle is hygienic. There is thus a need for cleaning strongly interlocked hair strands, which is currently difficult or not possible. There is thus a danger that the interlocked hair strands can come apart from within, can be damaged and even break off or fall out. Thus for the user, who wants to have a rasta hairstyle for a long time, a method is thus desirable, which permits the opening or separation of the strands after a certain time. Thus the desired rasta hairstyle can be set up a new after an intense hair cleaning and/or hair care treatment.

SUMMARY OF THE INVENTION

It is an object of the present invention to provide a method of setting up a temporary rasta hairstyle, which does not suffer from the above-described disadvantages and which can be removed later without damaging the hair.

It is a further object of the present invention to provide compositions for effectively performing the method of setting up a temporary rasta hairstyle according to the invention.

It is another object of the claimed invention to provide a multi-part kit for the method of setting up a temporary rasta hairstyle according to the invention.

It has now been found that these objects can be surprisingly attained by a method according to the invention of setting up a temporary rasta hairstyle and later removing it.

According to the invention this method includes one or more of the following steps:

a) applying one or more roughening substances to the hair to increase the roughness of the hair surface or applying at least one composition making back-combing easier;

b) applying one or more adhesion-increasing substances to the hair to increase adherence of hairs to each other; and c) setting up temporary rasta strands by intertwining the hair strand-wise, without essentially, i.e. irreversibly, interlocking the hairs.

The intertwining of the hair strands can occur e.g. either by gently back-combing or by one or more of dividing, drawing apart and twisting the divided hair strands, or by a combination of twisting the strands around their long axis and gently back-combing the twisted strands. The cleaning of the temporary rasta hair style can occur using a concave sponge, without destroying the hair style. In order to remove the temporary rasta hairstyle another composition, which increases the wet combability of the hair, is applied to the hair. The rasta strands are opened and/or unwound, preferably mechanically using an ordinary comb or brush.

It was surprisingly found that it is possible to produce an authentic or an at least nearly authentic rasta-look or rasta appearance, like a "true" permanent rasta, without damaging the hair and without the up to now strongly irreversibly interlocked hairs considered as a prerequisite. Furthermore it was surprising that the removal of the rasta hairstyle is possible simply without problems. The hair makes an even better cared for and healthier impression than prior to treatment after removal of the temporary rasta hairstyle, especially regarding the feel, luster and combability. This is immediately astonishing, since up to now a rasta hair style is almost synonymous with strongly damaged and uncared for hair. Now with the methods according to the invention the opposite has been achieved. The care action is partially what one would have expected from the action of the remover composition C that is described in detail hereinbelow. This means that it is based on a synergistic care action of the remover composition C in combination with the pre-treatment compositions A and/or B described in more detail below.

The subject matter of the invention is thus a method of setting up a temporary rasta hairstyle, in which, prior to or after putting the hair in the hairstyle, at least one of the following process steps occurs: (1) applying to the hair surface at least one roughening substance for roughening the hair surface or at least one composition for making back-combing of the hair easier and (2) applying to the hair tips or the hair at least one substance increasing adherence of the hairs to each other. The term "temporary rasta hairstyle" means a hairstyle with the appearance of a rasta look, which is again removable in contrast to a permanent rasta hairstyle. In contrast to the permanent rasta hairstyle the hair is not essentially or substantially interlocked, but only intertwined, i.e. the hairs that are twisted together can be mechanically separated from each other again. The roughening substance that increases the roughness of the hair surface is a substance, which adheres to the hair surface and causes clean hair to feel rough or dull in contrast to hair that has not been treated. This substance can be applied to the hair by means of composition A, which is described in more detail hereinbelow.

The stability of the temporary rasta hairstyle is clearly increased when an adhesion-increasing substance that increases the adherence of the hairs with each other is applied to hair and/or to the hair tips that has or have been pre-treated with the roughening substance increasing the surface roughness. The application of the adhesion-increasing substance increasing the adhesion of the hairs with each other can occur by means of the composition B that is described in more detail hereinbelow. The adhesion-increasing substance can be applied either prior to or after setting up the rasta hairstyle as necessary.

Setting Up of the Temporary Rasta Hairstyle

To set up the temporary rasta hair style hairs that are predetermined according to the invention are arranged or put in one or more temporary dreadlocks. This can occur by several methods. One of the three following methods is recommended for doing this. The recommended methods are to be understood as exemplary embodiments. In all of these techniques the setting up of the dreadlocks begins on the neck. Moreover one section (for example of about three cm thick) is divided from side to side transversely to the head. The base surface of the individual dreadlocks (individual strands) depends on the desired thickeness/density, amounting usually to 6 to 9 $cm^2$ and can be square, rectangular, trapezoidal or triangular. One works in the direction of the forehead in these methods or techniques. The dreadlocks are laid over each other in the manner of shingles. In order to improve the planed hairstyle, the dreadlocks are preferably held directly in the desired direction during setting up of the hairstyle.

Especially Preferred Methods

The separated individual strand is uniformly gently back-combed (intertwined, not interlocked) with a back-comb from the hair roots to the hair tips. During the back-combing the individual strand is twisted over its long axis, whereby a special round and "true" appearing dreadlock is produced. Instead of a back-comb also any suitable tool, for example a brush or currycomb with bristles, teeth or prongs made of metal, hard plastic or the like can be used.

Additional Preferred Methods

The separated or divided individual strand is strongly twisted with the fingers over its long axis. After 2 to 3 twists the hair strand is arbitrarily divided at the tips. Both hair strands arising by the division are now spread from each other, whereby the two to three prior twists move toward the hair roots and intertwine (similar to back bombing). The twist, division and spreading of the hair strand is performed until the entire length of the individual strand is intertwined.

Additional Possible Methods

The separated or divided individual strand is strongly twisted with the fingers over its long axis, until the entire strand is effectively "knurled". The hair tips of the hair strand are held fixed and the spreading on the long axis is somewhat reduced. Now the already twisted strand is gently back-combed with a suitable back-comb, without interlocking the hairs. The back-combing occurs over the entire axial length of the individual strand. After that the twisted and back-combed strand is rolled between the thumb and index finger once more in order to augment the intertwining effect.

Composition A

The application of the roughening substance increasing the roughness of the hair surface can occur by means of a first composition A (A1, A2). Suitable substances are e.g. those substances, which are solid at room temperature (25° C.) and are present in the form of particles. Silica, silicates, aluminates, clays, micas, salts, especially inorganic metal salts, metal oxides, e.g. titanium dioxide, minerals and polymers are somewhat suitable. Polymers, which impart a rough dull feel to the hair, are suitable. The suitability of a polymer is established by half-side tests of polymerically treated hair in contrast to untreated hair.

Suitable roughening polymers are, for example, copolymers of alkylacrylamides, especially $C_1$-$C_8$-alkyl groups, and at least one monomer selected from the group consisting of acrylic acid, methacrylic acid and their simple esters, especially the $C_1$-$C_4$-alkyl esters (INCI: acrylates/octylacrylamide copolymer, acrylates/t-butylacrylamide copolymer, e.g. AMPHOMER® HC and/or ULTRAHOLD® 8); copolymers of vinyl methyl ether and alkyl hemiesters of maleic acid, especially $C_1$-$C_5$-alkyl hemiesters (INCI: butyl ester of PVM/MA copolymer, e.g. GANTREZ® ES 425; copolymers of vinyl acetate and crotonic acid (INCI: VA/crotonates copolymer, e.g. LUVISET® CA 66).

The roughening substance can be present in the form of solid particles in the composition A and preferably the solid particles are dispersed in the composition to form a stable dispersion. Alternatively they can be present in dissolved form in a suitable cosmetically acceptable solvent. They are then separated from the solution after applying the solution to the hair and evaporating the solvent. A stable dispersion can be attained, when the composition A is provided with a flow limit, which is sufficiently large, in order to prevent the settling of the solid particles. This flow limit can be adjusted to a suitable value by using a suitable gel former.

Silica (silica gel, silicon dioxide) and metal salts, especially inorganic metal salts, are especially preferred as the roughening substance applied to the hair. Silica is most preferred. The metal salts include, e.g., alkali or alkaline earth metal halides, such as sodium chloride and potassium chloride; alkali or alkaline earth sulfates, such as sodium sulfate or magnesium sulfate. In the event that a soluble metal salt is used composition A is preferably an aqueous solution of this salt and is preferably in combination with a spraying device, e.g. a mechanically operated spray pump. In case insoluble particles are used, which are not soluble in water, alcohol and/or an alcohol/water mixture, such as silicon dioxide or a metal oxide, composition A is preferably a gel having a flow limit or yield point and contains at least one gel former that establishes the flow limit. Alternatively composition A is a foamable composition containing at least one foam-forming surfactant and/or foam-forming polymer. The foaming can occur by an aerosol propellant or by means of a mechanically operated apparatus for making foam.

In the case of the embodiments of composition A that are gel, thickening polymers are included, which impart a plastic or pseudo-plastic behavior to the compositions. The Theological flow properties of the gel according to the invention are characterized by the existence of a flow limit. The flow limit preferably amounts to at least 3 Pascal, measured with a Haake Rotation Viscometer RV 12, measurement system PKV-0.5 at 30° C. and at a linearly increasing shear rate of 0 to 100 s$^{-1}$. After exceeding the flow limit the gel preferably has a viscosity of 1,000 to 100,000 mPa·s, especially from 5,000 to 50,000 mPa·s at 25° C., measured with a Haake Rotation Viscometer Type VT 501 at a shear rate of 12.9 per second. The flow point or flow limit is selected according to weight and surface area of the particles so that it is at least as large as the pressure exerted by the particles. The settling of the particles is thereby prevented. The thickeners are preferably contained in an amount of from 0.05 to 10, especially preferably from 0.1 to 4, percent by weight, in composition A. The optimum concentration is dependent on the type of thickener and the weight of the particles. Suitable thickeners are cross-linked or not cross-linked polyacrylic acids or polymethacrylic acids. These thickeners, which can be contained in the compositions according to the invention, include homopolymers of acrylic acid with a molecular weight of 2,000,00 to 6,000,000 g/mol, which are marketed e.g. by Goodrich, USA under the trademark CARBOPOL®. Additional thickeners are e.g. the acrylic acid polymers, acrylic acid/acrylamide copolymers or Sclerotium Gum, marketed under the trademark MODAREZ® V 600 PX of Protex, France or under the trademark CARBOPOL® ETD 2001 by Goodrich, USA. Copolymers of acrylic acid or methacrylic acid, such as those marketed under the trademark CARBOPOL® 1342 or PEMULEN® TR1 of Goodrich, USA, are suitable. Guar gum, xanthan gum, bentonite and hectorite are additional suitable thickeners. In an advantageous embodiment of the composition thickeners are included in the composition besides those that impart a sufficient flow limit or flow point in the viscosity range typical for gels in addition to those thickeners that impart a sufficient flow limit or flow point to the composition. These latter thickeners include especially cellulose and cellulose derivatives, such as carboxymethyl cellulose, cellulose ether and hydroxyalkyl cellulose compounds, such as hydroxyethyl cellulose and hydroxypropyl cellulose. The thickeners contain acid groups, which are at least partially neutralized with cosmetically compatible bases. Suitable organic or inorganic bases that are appropriate for cosmetic applications can be used as the neutralizing agents. For example, the bases can include amino alcohols, such as aminomethylpropanol (AMP), triethanolamine or monoethanolamine and ammonia, NaOH and others.

Composition A also can be in the form of an aerosol or non-aerosol sprayable or foamable product. The aerosol products include a pressure-tight aerosol container with a spray or foam head, which contains the foamable or sprayable composition. The pressure-tight aerosol container of the aerosol spray product according to the invention can be made from any material known for aerosol spray or foam products. Metals, such as aluminum or tin, are especially suitable materials. Preferably the aerosol propellants are employed in an amount of from 1 to 20, especially preferably from 2 to 10, percent by weight. For example, lower alkanes, such as n-butane, i-butane, propane, butane, or also their mixtures and dimethyl ether or fluorohydrocarbons, such as F 152a (1,1-difluoroethane) or F 134 (tetrafluoroethane) are suitable as the aerosol propellants. In addition, propellants present in compressed gaseous form, such as $N_2$, $N_2O$ and $CO_2$, and their mixtures are suitable as the propellants.

Preferably the composition comprises an aqueous or an aqueous-alcoholic medium with preferably at least 10 percent by weight water. The solvent system is preferably present in the composition in an amount of 50 to 98, especially preferably from 75 to 95, percent by weight. The alcohols included in the solvent system especially include lower alcohols having one to four carbon atoms that are suitable for cosmetic purposes, such as ethanol and isopropanol. Organic solvents or mixtures of solvents with a boiling point under 400° C. are suitable as co-solvents in amounts of from 0.1 to 15, especially from 1 to 10, percent by weight. Branched or unbranched hydrocarbons, such as pentane, hexane, isopentane and cyclic hydrocarbons, such as cyclopentanes and cyclohexane, are suitable as additional co-solvents. Glycerol, ethylene glycol and propylene glycol are additional especially suitable water-soluble solvents.

In the case of non-aerosol sprays and non-aerosol foams, the compositions are present in combination with a mechanically operated apparatus for spraying or forming.

The foamable products usually contain at least one foam-producing substance, e.g. a foam-forming surfactant and/or a foam-forming polymer. The surfactant can have nonionic, anionic or amphoteric character. Nonionic foam-forming surfactants are preferred. The surfactants can be used individually or in a mixture. The amount of the surfactants can be varied and is selected so that a sufficient amount of foam is formed for working into the hair, when the composition is delivered from the aerosol container or the product dispenser. The surfactant amount is preferably typically from 0.01 to 5, especially preferably from 0.1 to 2, percent by weight. Suitable nonionic surfactants are, for example, the $C_8$-to $C_{18}$-fatty alcohols, which can be ethoxylated with from 8 to 45 mol ethylene oxide, e.g. lauryl alcohol, tetradecyl alcohol, cetyl alcohol, oleyl alcohol or stearyl alcohol, ethoxylated with up to 40 mol ethylene oxide per mol fatty acid, alone or in a mixture; hydrogenated castor oil ethoxylated with 8 to 45 mol ethylene oxide; $C_8$-to $C_{18}$-fatty acid alkanolamides; fatty alcohols of ethoxylated lanolin orethoxylated lanolin; polyglyceryl ethers of saturated or unsaturated fatty alcohols and alkyl phenols with 8 to 30 carbon atoms in alkyl groups and with 1 to 10 glyceryl units per molecule; polyethylene/polypropylene block copolymers and ethoxylated sorbitan fatty acid ester. Derivatives of natural surfactants, e.g. alkylpolyglycosides, are especially preferred as the nonionic surfactants. For example, alkyl sulfates, alkyl ether sulfates, alkyl sulfonates, alkoyl sarcosinates, akly isethionate or dialkylsulfosuccinates, which contain from 8 to 18 carbon atoms, are suitable anionic surfactants. Betaines are especially suitable as amphoteric surfactants. For example, the betaines include $C_8$-to $C_{18}$-alkyl betaines, such as cocodimethylcarboxymethylbetaine, lauryldimethylcarboxymethylbetaine, lauryldimethyl-alpha-carboxyethylbetaine, cetyldimethylcarboxymethylbetaine, oleyldimethyl-gamma-carboxypropylbetaine and lauryl-bis-(2-hydroxypropyl)-alpha-carboxyethylbetaine; $C_8$-to $C_{18}$-sulfobetaines, such as cocodimethylsulfopropylbetaine, stearyidimethylsulfopropylbetaine, lauryldimethylsulfoethylbetaine, lauryl-bis-(2-hydroxyethyl)sulfopropylbetaine; the carboxyl derivatives of imidazoles, the $C_8$-to $C_{18}$-alkyldimethyl ammonium acetates, the $C_8$-to $C_{18}$-alkyldimethyl carboxymethyl ammonium salts and the $C_8$-to $C_{18}$-fatty acid alkylamidobetaines, such as coconut fatty acid amidopropylbetaine, and N-coconut fatty acid amidoethyl-N-[2-(carboxy-methoxy)ethyl]glycerol (CTFA: cocoamphocarboxyglycinate).

The back-combing of the hair can also be made easier by treatment with compositions, such as corn soap or permanent wave shaping compositions containing hair keratin reducing compounds. The use of permanent shaping means occurs preferably under mild conditions, in which the hair is not greatly damaged, e.g. with smaller effective ingredient concentrations and/or short acting times. The permanent shaping agents contain hair keratin reducing agents, which act by opening the cystine disulfide bridges of the hair keratin. Effective reducing agents include especially thio compounds, such as salts of sulfur containing acids or certain mercapto compounds, especially salts or esters of mercaptocarboxylic acids. The classical permanent shaping agent in the art, namely thioglycolic acid, or its ammonium or monoethanolamine salt, can also be used in the methods according to the present invention. Additional conventional reducing agents are inorganic sulfite, 2-mercaptopropionic acid (thiolactic acid), 3-mercaptopropionic acid, mercaptocarboxylic acid ester, mercaptocarboxylic acid amide, cysteine and derivatives of these compounds. The salts or derivatives of mercaptocarboxylic acid, especially thioglycolic acid, cysteine and thiolactic acid or their salts, are particularly preferred.

The permanent shaping effective ingredient can be used in an amount of from 2 to 30 percent by weight. The lower concentrations are generally preferred up to a maximum of 20 percent by weight, especially up to a maximum of 10 percent by weight.

One composition can be made available, which is universally suitable by variation of pH for any hair structure, if necessary with additional heating action. The composition is adjusted to be either acidic (with sulfite, bisulfite and mercaptocarboxylic acid ester) or alkaline (with alkali and ammonium salts of mercaptocarboxylic acid). Alkalizing agents are used to adjust the pH to e.g. 7 to 10, especially 7 to 8.5. These alkalizing agents include ammonia, soda lye, organic amines, e.g. monoethanolamine, and also all other water-soluble, physiologically compatible basically reacting, organic or inorganic salts, such as ammonium or alkali carbonates and ammonium or alkali hydrogen carbonates. In order to adjust the pH of the composition so that the composition is acidic (e.g. pH=6.5 to 6.9), esters of mercaptocarboxylic acids, e.g. monothioglycolic acid glycol ester or monothioglycolic acid glyceryl ester, preferably mercaptoacetamide or 2-mercaptopropionic acid amide, in a concentration of 2 to 14 percent by weight; or the salts of sulfur-containing acids, e.g. sodium-, ammonium-or monoethanolammonium sulfite, in a concentration of 3 to 8 percent by weight (calculated as $SO_2$) can be used.

The permanent shaping composition used in the methods of the invention can be present in the form of an aqueous solution or an emulsion as well as in thickened form on an aqueous basis, especially as a cream, gel or paste. It is particularly preferable that it is in viscose form with a consistency that permits the hair to be treated in place and not, as is common in the art, in a wash basin. A viscosity of from 100 to 10,000, preferably from 300 to 1000, mPa s at 25° C. is especially preferred. The stated viscosity limits relate to a measurement with a Haake Rotation Viscometer Type VT 501 with a shear rate of 64.5 per second. Similarly it is possible to fill these compositions in an aerosol can under pressure and to dispense them as aerosol foam.

A so-called swelling and penetration agent can be included in the permanent shaping composition to increase its effectiveness. Swelling and penetration agents include, e.g., urea, polyhydric alcohols, ether, melamine, alkali or ammonium thiocyanate, isopropanol, dipropylene glycol monomethyl ether, 2-pyrrolidone, imidazolidin-2-one or 1-methyl-2-pyrrolidone in an amount of about 0.5 to 50 percent by weight, preferably 2 to 30 percent by weight. To avoid overcurling of hair dithio compounds, especially dithiols, dithiodiglycolic acid, dithiolactic acid, or the respective salts of the dithiols are added.

During application the hair can be washed with a shampoo and after that rinsed with water. Subsequently the hand towel dried hair can be divided into individual strands and only individual strands are treated when only a partial rasta hair style is to be set up. Then the hair is treated with the agent or composition in a sufficient amount, preferably from 60 to 120 grams. After a sufficient acting time, which depends on the hair nature, pH and action of the permanent shaping composition, as well as on application temperature, namely from 2 to 30 minutes (5 to 30 minutes without heat; 2 to 20 minutes with heating), the hair is rinsed with water. The shorter acting times, for example up to 15 minutes or up to 10 minutes without heating or up to 10 or 7 minutes with heating, are preferred.

Composition B

The application of the adhesion-increasing substance causing the hairs to adhere to each other can occur by means of a second composition B. Suitable substances are, e.g., waxes, waxy materials and/or adhesive polymers. Waxes and waxy materials are especially those substances with the properties according to the definition of waxes in Ullmanns' Encyclopedia of Industrial Chemistry, $4^{th}$ Edition, Volume 24, page 3. According to this Encyclopedia the waxes are kneadable at 20° C., solid to brittle and hard, fine to gross crystalline, at least translucent to opaque, however not glassy, melting over 40° C. without decomposition, comparatively low viscosity a little over its melting point, strongly temperature dependent in its consistency and solubility and polishable under a gentle pressure. In the following the terms "wax substance" and "waxy or wax-like substance" are synonymous in the following. Adhesive polymers, which are suitable, include those polymers, which impart an adhesive feel to the hair, as established by half-side tests of polymerically treated hair in comparison to untreated hair.

Suitable hydrophobic waxes include animal, plant, mineral and synthetic waxes, microcrystalline waxes, solid paraffins, petrolatum, VASELINE®, ozokerite, montan wax, Fischer-Tropsch wax, polyolefin waxes, for example polybutene, beeswax, wool wax and its derivatives, e.g. wool wax alcohols, candelilla wax, carnauba wax, Japan wax, hardened fats, fatty acid esters and fatty acid glycerides with a solidification point of over 40° C., polyethylene waxes and silicone waxes. The waxes have a solidification point of over 40° C., preferably over 55° C. The needle penetration number (0.1 mm, 100 g, 5 s, 25° C., according to DIN 51 579) is preferably in a range of from 2 to 70, especially from 3 to 40, especially preferably less than 20. Carnauba wax, ceresin wax and their mixtures are especially preferred. The waxes and waxy materials in composition B are preferably contained in an amount of from 4 to 50, especially preferably from 8 to 30, and particularly preferably from 10 to 25, percent by weight.

The composition B containing the adherence-improving substance for promoting the adherence of the hairs with each other can be present in various application forms, especially a lotion, gel, aerosol spray, non-aerosol pump spray, aerosol foam, non-aerosol foam product or as a solid or semi-solid wax product in a dish or in the form of a pencil.

In an especially preferred embodiment composition B is an aqueous emulsion of a hydrophobic wax and contains at least one emulsifier and water in addition to the wax. The term "emulsion" includes wax dispersions in water, but also suspensions of solid wax particles in water. The emulsifiers are, preferably, contained in an amount of 0.5 to 50, especially from 3 to 40, and particularly from 20 to 35, percent by weight. Preferably the emulsifiers are nonionic surfactants. The following emulsifiers are especially suitable:

- addition products of 2 to 30 mol ethylene oxide and/or 1 to 5 mol propylene oxide to $C_8$-to $C_{22}$-fatty alcohols, to $C_{12}$-to $C_{22}$-fatty acids or to alkanol phenols with $C_8$-to $C_{15}$-alkyl groups;
- $C_{12}$-to $C_{22}$-fatty acid monoesters or diesters of addition products of from 1 to 30 mol ethylene oxide to glycerol;
- addition products of 5 to 60 mol ethylene oxide to castor oil or to hardened (hydrogenated) castor oil; and
- mon-, di-and triesters of phosphoric acid with addition products of 2 to 30 mol ethylene oxide to $C_8$-to $C_{22}$-fatty alcohols.

In an especially preferred embodiment the total amount of the emulsifiers present is larger than the total amount of the waxes. That means that the weight ratio of the emulsifier to wax is larger than 1:1, preferably up to 5:1, especially preferably from 1.5:1 to 3:1. These embodiments are characterized by a combination of individual active ingredients. Directly after the application to the hair the adhesion force of the hairs is very high, which very much simplifies the setting up of a rasta hairstyle. After drying the adherence is greatly reduced, which leads to an improved pleasant feel. A reduced, not unpleasant, residual adhesion remains and causes the finished rasta strands to adhere loosely to each other, which provides additional fresh hair styling possibilities. The preferably advantageous automatically decreasing adhesion force is especially strongly expressed in combination with silica as the roughening substance that increases the roughness of the hair. An additional especially advantageous effect is the sufficiently good residue less removal of the hydrophobic wax, especially using the composition C described further below for removing the rasta hairstyle. Composition B is present ideally in liquid, i.e. liquid or viscous form. It is preferably dispensed in liquid form by means of a pumping device, sprayed as a spray by means of a spraying device or as foam with an apparatus for producing foam. For additional ingredients for the aerosol and non-aerosol embodiments reference is made to the similar ingredients described above as suitable for composition A.

As waxes however hydrophilic waxes can be used, especially high molecular weight polyethylene glycols (PEG). The polyethylene glycols are preferably waxy solids at room temperature (20 to 25° C.) or at least soft waxy-like compositions with a solidification temperature at about 30° C., preferably at about 40° C. The molecular weight amounts to preferably from 850 to about 5000 g/mol, especially preferably from 1200 to 3500 g/mol. Polyethylene glycols have the general formula $H(OCH_2CH_2)_nOH$. Suitable high molecular weight polyethylene glycols are, e.g., those with n=19 to 113, preferably with n=30 to 79. Suitable polyethylene glycols have the INCI-name PEG-20 (n=20), PEG-32 (n=32), PEG-60 (n=60), PEG-75 (n=75), PEG-90 (n=90) and PEG-100 (n=100). Commercial products usually have a molecular weight distribution. Suitable commercial products are, e.g., polyglycol 1000, polyglycol 1350, polyglycol 1500, polyglycol 3000 or polyglycol 4000 of Clariant. The numerical values designate approximately the average molecular weight.

In an additional preferred embodiment the adherence increasing composition B is a microemulsion. The microemulsion is formed from a hydrophobic oil ingredient that is liquid at ambient temperature (20° C.), an emulsifier and water. It also can contain an adhesive polymer. The emulsifier can be any of the above-mentioned emulsifiers in the above-mentioned amounts. Any of the oil ingredients that are known to those skilled in the art can be used. Plant or animal oils, mineral oils, silicone oils or their mixtures can be used as the oils. Suitable silicone oils include polydimethylsiloxanes, phenylated silicones, polyphenylmethylsiloxanes, phenyltrimethicones, poly($C_1$-$C_{20}$)alkylsiloxanes, alkylmethylsiloxanes. Also hydrocarbon oils, such as parallin or isoparaffin oils, squalane, oils from fatty acids and monoalcohols or polyols, especially fatty acid esters and fatty acid triglycerides. Suitable plant oils are, e.g., sunflower seed oils, coconut oil, castor oil, lanolin oils, jojoba oil, corn oil and soybean oil. Hydrocarbon oils, especially mineral oils (*Paraffinum liquidum*), and fatty acid triglycerides, wherein the fatty acids have at least eight carbon atoms, are especially preferred. The oil ingredient is preferably contained in an amount of from 0.1 to 25 percent by weight, especially preferably from 1 to 10 percent by weight.

The adhesive polymers are preferably contained in an amount of from 0.1 to 25 percent by weight, especially preferably from 1 to 10 percent by weight. The adhesive polymers can be homopolymers or copolymers based on acrylates and/or acrylamides, i.e. polymers, in which at least one monomer is selected from the group consisting of acrylic acid, methacrylic acid, acrylic acid esters, methacrylic acid esters, acrylamides, methacrylamides, alkylacrylamides and alkylmethacrylamides, in which the alkyl groups preferably include from one to five carbon atoms.

Rast-Cleaning

To care for the temporary rasta hairstyle as-careful-as-possible a cleaning without greatly mechanically stressing the rasta strands is recommended. Careful cleaning comprises moistening the hair and then applying a hair cleaning composition, which contains at least one wash-active surfactant, to the hair or a sponge. Then the composition is cautiously distributed on the hair, e.g. by dabbing with the sponge. Subsequently the cleaning composition is removed from the hair, which occurs by rinsing with water or by dabbing with the sponge after rinsing it many times in the meantime. The sponge preferably has a concave shape. The concave shape approximately corresponds to the shape of the head. The application, distribution and/or removal of the cleaning composition on the hair occur with the concave inner side of the sponge.

Rasta-Removal

The removal of the temporary rasta-hairstyle set up according to the invention can occur by moistening the hair, applying a remover composition C to the hair and distributing it on the hair. The rasta strands are then opened or unwound. Finally the composition C can be rinsed from the hair.

Composition C

The composition C contains at least one substance that increases the wet or moist combability. This combability increasing substance is preferably contained in the composition C in an amount of from 0.01 to 10, especially preferably from 0.05 to 5, percent by weight. For example, cationic polymers, cationic surfactants, amine oxides, cationic silicone compounds, oil ingredients, fatty alcohol and glycerol fatty acid monoesters, are suitable. Suitable cationic surfactants include those, which contain a quaternary ammonium group and at least one organic residue with at least six carbon atoms. Suitable carionic surfactants can be of the general formula:

$$N^{(+)}R^1R^2R^3R^4X^{(-)}$$

wherein $R^1$ to $R^4$ each represent, independently of each other, an aliphatic group, an aromatic group, an alkoxy group, a polyoxyalkylene group, an alkylamido group, a hydroxyalkyl group, an aryl group or alkylaryl group, each of the foregoing groups having from 1 to 22 carbon atoms, wherein at least one of the groups has at least six carbon atoms and X represents an anion. The anion can be a halogen anion, acetate, phosphate, nitrate or alkyl sulfate, preferably a chloride anion. The aliphatic group can contain cross-linking or other groups, such as amino groups, in addition to the carbon and hydrogen atoms. The groups can be linear, branched or cyclic. For example, the following are suitable cationic surfactants: the chlorides or bromides of alkyldimethylbenzyl ammonium salts, of alkyltrimethyl ammonium salts, for example cetyltrimetyl ammonium chloride or bromide, tetradecyltrimetyl ammonium chloride or bromide, alkyldimethylhydroxyethyl ammonium chloride or bromide, the dialkyldimethyl ammonium chloride or bromide, alkylpyridinium salts, especially lauryl or cetylpyridinium chloride, alkylamidoethyltrimethyl ammonium ether sulfate and compounds with cationic character, such as amine oxides, for example, alkylmethylamine oxide or alkylaminoethyldimethylamine oxide with at least six carbons in the alkyl groups. Cetyltrimethyl ammonium chloride is particularly preferred as the cationic surfactant.

Cationic polymers in the sense or the present invention are those polymers, which contain at least one cationic or cationizable group that becomes a cationic group when protonated. Cationic groups, for example, include quaternary amine groups. Cationizable groups, for example, include primary, secondary or tertiary amine groups. The cationic polymers can be homopolymers or copolymers, in which the cationic or cationizable groups are either in the polymer chain or preferably present as substituents on one or more of the monomers.

Suitable monomers of the cationic polymer, which have cationizable groups, are unsaturated radically polymerizable compounds, which have at least one neutralized or not neutralized basic group. The basic groups can include especially primary, secondary or tertiary amine groups. The amine nitrogen can also be part of a ring. For example, the monomers of this type include monoalkylaminoalkylacrylates or -methacrylates and dialkylaminoalkylacrylates or -methacrylates. The alkyl groups of these monomers are preferably lower alkyl groups, such as $C_1$-to $C_7$-alkyl groups, especially preferably $C_1$-to $C_4$-alkyl groups.

Suitable monomers, which have quaternary amine groups, are unsaturated radically polymerizable compounds, which have at least one quaternary amine group. These monomers preferably include ammonium substituted vinyl monomers or quaternarized derivatives of carboxy vinyl monomers, such as quaternarized acrylamides or methacrylamides. For example, acrylamidoalkyltrialkyl ammonium halides or methacrylamidoalkyltrialkyl ammonium halides, trialkylmethacryloxyalkyl ammonium halides, trialkylacryloxyalkyl ammonium halides, dialkyldiallyl ammonium halides or quaternary vinyl ammonium monomers with groups containing cyclic, cationic nitrogen, such as pyridinium, imidazolium or quaternary pyrrolidone, e.g. alkylvinylimidazolium, alkylvinylpyridinium, or alkylvinylpyrrolidone salts, are suitable. The alkyl groups of these preferred monomers preferably include lower alkyl groups, such as $C_1$-to $C_7$-alkyl groups, especially preferably $C_1$-to $C_3$-alkyl groups. Acrylamidopropyltrimethyl ammonium chloride and methacrylamidopropyltrimethyl ammonium chloride are particularly preferred.

The cationic polymer can be polymerized, as needed, with neutral comonomers, which contain neither cationic nor cationizable groups. For example, the following comonomers are suitable: acrylamides, methacrylamides, alkylacrylamides, dialkylacrylamides, alkylmethacrylamides, dialkylmethacrylamides, alkylacrylates, alkylmethacrylates, vinylcaprolactone, vinyl pyrrolidone, vinyl ester, vinyl alcohol, propylene glycol or ethylene glycol. The alkyl groups in these comonomers preferably contain $C_1$-to $C_7$-alkyl groups, especially preferably $C_1$-to $C_3$-alkyl groups.

For example, the following are suitable cationic polymers: polyvinylpyrrolidone/dimethylaminoethylmethacrylate copolymers, copolymers of polyvinylpyrrolidone and imidazolimine methochloride, the terpolymer of dimethyldiallylammonium chloride, sodium acrylate and acrylamide, the terpolymer of vinyl pyrrolidone, dimethylaminoethyl methacrylate and vinyl caprolactam, quaternary ammonium salts of hydroxyethyl cellulose (INCI name: polyquaternium-10 or polyquaternium-24), cationic guar derivatives, vinyl pyrrolidone/methacrylamidopropyltrimethyl ammonium chloride copolymers or diquaternary polydimethylsiloxane (INCI name: Quaternium-80), stearyldimethylammonium hydroxyethyl cellulose, methacryloyl ethyl betaine/methacrylate copolymers, polymethacrylamidopropyl trimonium chloride, Polyquaternium-2, Polyquaternium-6, Polyquaternium-7, Polyquaternium-18, Polyquaternium-22, Polyquaternium-27, Polyquaternium-39 and polymers with siloxane units, e.g. Polyquaternium-41 or Polyquaternium-42.

Chitosan or a chitosan derivative, which is neutralized with a cosmetically compatible acid, is also suitable as a cationic polymer. The cosmetically compatible acid can be an inorganic or organic acid, e.g. formic acid, tartaric acid, malic acid, maleic acid, fumaric acid, pyrrolidone carboxylic acid, citric acid, lactic acid, sulfuric acid, acetic acid, hydrochloric acid, phophoric acid, among others. Suitable chitosan derivatives include, for example, quaternary alkylated or hydroxyalkylated derivative compounds, for example, hydroxyethyl chitosan, hydroxypropyl chitosan or hydroxybutyl chitosan. The chitosan or chitosan derivative preferably has a molecular weight of 20,000 to 5,000,000 g/mol. For example, a low molecular weight chitosan have a molecular weight of from 30,000 to 70,000 g/mol or a high molecular weight chitosan having a molecular weight of from 300,000 to 700,000 g/mol are suitable. The preferred deacetylation degree of the chitosan is between 10 to 99 percent. The neutralization degree for the chitosan or the chitosan derivative is preferably at least 50 percent, especially preferably from 70 to 100 percent, in relation to the number of free base groups.

Suitable cationic polymers, which are derived from natural polymers, include cationic derivatives of polysaccharides, for example cationic derivatives of cellulose, starches or guar. Additional chitosan and chitosan derivatives are also suitable. The suitable cationic derivatives of polysaccharides have the general formula:

$$G-O-B-N^+R^aR^bR^cX^-$$

wherein G is an anhydroglucose group, for example a starch or cellulose anhydroglucose;

B is a divalent group, for example alkylene, oxyalkylene, polyoxyalkylene or hydroxyalkylene;

$R^a$, $R^b$ and $R^c$ are each, independently of each other, alkyl, aryl, alkylaryl, arylalkyl, alkoxyalkyl or alkoxyaryl with up to 18 carbon atoms, respectively, wherein the total number of carbon atoms in each of these groups is preferably a maximum of 20;

$X^-$ is a customarily used or ordinary counter ion, for example a halide, an acetate, a phosphate, a nitrate or an alkylsulfate, preferably a chloride. A cationic cellulose is marketed under the trademark POLYMER JR® of Amerchol and has the INCI name Polyquaternium-10. Additional cationic cellulose has the INCI name Polyquaternium-24 and is marketed under the tradename Polymer LM-200 of Amerchol. A suitable cationic guar derivative compound is marked under the trademark JAGUAR R® and has the INCI name Guar Hydroxypropyltrimonium Chloride.

Those polymers are preferred, which have sufficient solubility in water, lower alcohol having one to four carbon atoms or their mixtures, so that they are present in the composition of the invention in completely dissolved form. The cationic charge density is preferably from 1 to 7 meq/g.

Suitable cation-active silicone compounds preferably have either at least one amino group or at least one ammonium group. Suitable silicone polymers with amino groups are known by the INCI name, amodimethicone. Amodimethicones are polydimethyl siloxanes with aminoalkyl groups. The aminoalkyl groups can be side chains or terminal groups. Suitable aminosilicones are those of the general formula:

wherein $R^8$, $R^9$, $R^{14}$ and $R^{15}$, independently of each other, are equal or different and each represent $C_1$-to $C_{10}$-alkyl, phenyl, hydroxy, hydrogen, $C_1$-to $C_{10}$-alkoxy or acetoxy, preferably $C_1$-to $C_4$-alkyl, especially preferably methyl;

$R^{10}$ and $R^{16}$ are the same or different and, independently of each other, represent $-(CH_2)_a-NH_2$ with a 1 to 6, $C_1$-to $C_{10}$-alkyl, phenyl, hydroxy, hydrogen, $C_1$-to $C_{10}$-alkoxy or acetoxy, preferably $C_1$-to $C_4$-alkyl, especially preferably methyl;

$R^{11}$, $R^{12}$ and $R^{13}$ are the same or different and independently of each other each represent hydrogen, a $C_1$-to $C_{20}$-substituted hydrocarbon group with at least one O and/or N atom substituent and an $C_1$-to $C_{20}$-unsubstituted hydrocarbon group, preferably a $C_1$-to $C_{10}$-alkyl or phenyl group, especially preferably a $C_1$-to $C_4$-alkyl group, most preferably methyl;

Q represents $-A-N-R^{17}R^{18}$, or $-A-N^+R^{17}R^{18}R^{19}$, wherein A stands for a divalent $C_1$-to $C_{20}$-alkylene compound group, which can contain an O—, N— or OH substituent group, and $R^{17}$, $R^{18}$ and $R^{19}$, independently of each other, are equal or different and represent hydrogen, a $C_1$-to $C_{22}$-substituted hydrocarbon group, preferably a $C_1$-to $C_4$-alkyl or phenyl group.

Preferably Q stand for $-(CH_2)_3-NH_2$, $-(CH_2)_3NHCH_2CH_2NH_2$, $-(CH_2)_3OCH_2-CHOHCH_2NH_2$ and $-(CH_2)_3N(CH_2CH_2OH)_2$, $-(CH_2)_3-NH_3^+$ and $-(CH_2)_3OCH_2CHOH-CH_2N^+(CH_3)_2R^{20}$, wherein $R^{20}$ is a $C_1$-to $C_{22}$-alkyl group or a $C_1$-to $C_{22}$-hydroxyalkyl group. Also x represents a number between 1 and 10,000, preferably between 1 and 1000; and y represents a number between 1 and 500, preferably between 1 and 50.

The molecular weight of the amino-silicones is between 500 and 100,000 g/mol. The amine content (meq/g) is preferably in a range of from 0.05 to 2.3, especially preferably from 0.1 to 0.5.

Suitable silicone polymers with two terminal quaternary ammonium groups are known under the INCI name Quaternium-80. The silicone polymers are dimethylsiloxanes with two terminal aminoalkyl groups. The quaternary aminosilicones that are suitable have the following general formula:

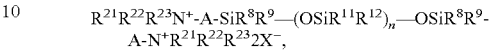

wherein A is a divalent $C_1$-to $C_{20}$-alkylene group or modified alkylene group containing O and N atoms and OH groups and is preferably $-(CH_2)_3OCH_2CHOH-CH_2N^+(CH_3)_2R^{20}$, wherein $R^{20}$ is a $C_1$-to $C_{22}$-alkyl residue, which can have an OH group substituent;

wherein $R^8$, $R^9$, $R^{11}$ and $R^{12}$ have the same significance as in the above silicone formula and are preferably methyl groups;

wherein $R^{21}$, $R^{22}$ and $R^{23}$, independently of each other, each represent a $C_1$-to $C_{22}$-alkyl residue, which can also contain hydroxy group substituents and wherein preferably at least one of the groups has at least 10 carbon atoms and the remaining groups have one to four carbon atoms; and n is a number from 0 to 200, preferably 10 to 100. These diquaternary polydimethylsiloxanes are marketed under the trademark ABIL® QUAT 3270, 3272 and 3274 of Goldschmidt, Germany.

Further suitable cation-active hair-care compounds are cationically modified protein derivative compounds or cationically modified protein hydrolyzates and for example are known under the INCI name lauryldimonium hydroxylpropyl hydrolyzed wheat protein, lauryldimonium hydroxypropyl hydrolyzed caesin, lauryldimonium hydroxypropyl hydrolyzed collagen, lauryldimonium hydroxypropyl hydrolyzed keratin, lauryldimonium hydroxypropyl hydrolyzed silk, lauryldimonium hydroxypropyl hydrolyzed soy protein or hydroxypropyltrimonium hydrolyzed wheat, hydroxypropyltrimonium hydrolyzed caesin, hydroxypropyltrimonium hydrolyzed collagen, hydroxypropyltrimonium hydrolyzed keratin, hydroxypropyltrimonium hydrolyzed rice bran protein, hydroxypropyltrimonium hydrolyzed silk, hydroxypropyltrimonium hydrolyzed soy protein, hydroxypropyltrimonium hydroxlyzed vegetable protein.

Suitable cationic derivatized protein hydrolyzates are mixed substances that can be obtained, for example, by reaction of alkaline, acidic or enzymatically hydrolyzed proteins with glycidyltrialkyl ammonium salts or 3-halo-2-hydroxypropyltrialkyl ammonium salts. Proteins, which act as starting materials for the protein hydrolyzates, can be of both vegetable or animal origin. Conventional starting materials are, for example, keratin, collagen, elastin, soy protein, rice protein, milk protein, wheat protein, silk protein or almond protein. A mixed material is produced by hydrolysis with molecular weights of from about 100 to about 50,000. Usually the average molecular weight is in a range of from about 500 to about 1000. Preferably the cationic derivatized protein hydrolyzates contain one or two long $C_8$-to $C_{22}$-alkyl chains and two or one short $C_1$-to $C_4$-alkyl groups. Compounds with the long alkyl chains are preferred.

Suitable fatty alcohols are alkyl alcohols with 8 to 22 carbon atoms, e.g. myristyl alcohol, cetyl alcohol or stearyl alcohol or their mixtures. The alkyl groups can be linear or branched. Suitable glycerol monofatty acid esters are monoesters of glycerol and the above-described fatty alcohols.

Suitable oils ingredients are, for example, plant or animal oils, mineral oils, silicone oils or their mixtures. Suitable silicone oils include polydimethylsiloxanes, phenylated silicones, polyphenylmethyl siloxanes, phenyltrimethicones, poly($C_1$-to $C_{20}$-)alkylsiloxanes and alkylmethylsiloxanes. Additional hydrocarbon oils, such as paraffin oils, isoparaffin oils, squalane, oils from fatty acids and polyols, are suitable. For example sunflower oils, coconut oils, castor oil, lanolin oil, jojoba oil, corn oil and soy oil are suitable. Hydrocarbon oils, especially mineral oil (*Paraffinum liquidum*), are particularly preferred.

Exemplary Composition C

The following O/W emulsion is a preferred example of the remover composition and contains:

(A) about 0.1 to 10 percent by weight, preferably from 0.3 to 5 percent by weight, of at least one cation-active hair care effective ingredient, preferably selected from the group consisting of cationic surfactants, cationic polymers and cationic silicone compounds;

(B) about 0.5 to 15 percent by weight, preferably from 1 to 10 percent by weight, of at least one hydrophobic fat or oil ingredient, preferably at least one fatty alcohol, fatty alcohol ester, natural oil, mineral oil or silicone oil; and (C) about 75 to 98 percent by weight, preferably from 80 to 95 by weight, water and auxiliary and additive ingredients, as needed, for example thickeners, multivalent alcohol, perfumes, dyestuffs, preservatives, acids and hair care ingredients.

Composition C can also be in the form of an aerosol product, especially aerosol foam. The above-described description regarding composition A provides a description of suitable required solvents and propellants for this sort of aerosol product.

Multi-Component Kits

The present invention also includes multi-component kits for performing the method according to the invention.

The kit according to the invention contains at least two components selected from
  an above-described composition increasing hair roughness;
  an above-described composition which increases adherence of the hairs to each other;
  a mechanical back-combing-assisting tool, e.g. a comb, especially a back-combing comb, a brush, a currycomb or an automatic back-combing or braiding machine for hair;
  a form-stable, concave sponge;
  at least one cleansing agent containing at least one wash-active surfactant;
  at least one composition containing at least one combability-increasing substance, preferably at least one cationic polymer, cationic surfactant, amine oxide, cationic silicone compound, oil ingredient, fatty alcohol or fatty alcohol ester, and/or
  at least one data recording medium, on which the steps of the method according to the invention are stored or recorded, as a whole or in part, in graphic, visual and/or audio form.

The kit according to the invention contains at least one first component, in which there is a composition that increases the roughness of the hair, and at least one second component, in which there is a composition which increases the adherence of the hairs with each other. This adherence-increasing composition contains either an emulsion comprising at least one hydrophobic wax, at least one emulsifier and water or at least one adhesive polymer or at least one hydrophilic wax. These compositions are comprised as described in the above description in detail. The first component preferably contains a composition, which includes at least one substance, which is silica, a silicate, an aluminate, a clay, mica, a salt, a metal oxide, a mineral and/or a polymer. Especially either an aqueous salt solution, which can be sprayed on the hair with a spraying apparatus or a foam-forming preparation, is preferred. These preferred preparations include silica, at least one foam-forming emulsifier, water and either at least one aerosol propellant or they are present in combination with a mechanical device for forming. The second component preferably includes an emulsion of at least one hydrophobic wax, at least one emulsifier and water.

Composition A, B and/or C can also contain from 0.01 to 15 percent by weight, preferably from 0.5 to 10 percent by weight, of at least one synthetic or natural non-ionic film-forming polymer, which preferably has a sufficient solubility in water or in a water-alcohol mixture, in order to be present in completely dissolved form. The term "film-forming polymer" means a polymer, which deposits a polymer film on the hair, when applied to the hair in a 0.01-to 5-percent aqueous, alcoholic or aqueous-alcoholic solution. Suitable synthetic, nonionic film-forming hair-fixing polymers are homo-or copolymers, which are built up from at least one of the following monomers: vinyl pyrrolidone, vinyl caprolcactam, vinyl esters, such as vinyl acetate, vinyl alcohol, acrylamide, methacrylamide, alkyl-and dialkylacrylamides, alkyl-and dialkylmethacrylamides, alkylacrylates, alkylmethacrylates, propylene glycol or ethylene glycol. The alkyl groups in these monomers preferably have from one to seven carbon atoms, especially preferably from one to three carbon atoms.

Suitable nonionic film-forming hair fixing polymers are, for example, homopolymers of vinylcaprolactam, of vinyl pyrrolidone or of N-vinylformamide. Additional suitable synthetic film-forming, nonionic, hair-fixing polymers are, for example, copolymerizates of vinyl pyrrolidone and vinyl acetate, terpolymers of vinyl pyrrolidone, vinyl acetate and vinyl propionate, polyacrylamides, polyvinyl alcohols and polyethyleneglycol/polypropyleneglycol copolymers. Polyvinyl pyrrolidones and copolymers of vinyl pyrrolidone and nonionic comonomers, especially polyvinyl pyrrolidoine/vinyl acetate copolymers, are particularly preferred. Suitable natural film-forming polymers are, e.g. cellulose derivatives, especially hydroxyalkyl cellulose compounds, such as hydroxypropyl cellulose.

The compositions of the invention can also include the following conventional cosmetic additive ingredients suitable for this type of hair treatment composition: e.g. perfume oils, in an amount of from 0.01 to 0.5 percent by weight; propellants, e.g. ethylene glycol distearate, in an amount of about 0.2 to 5.0 percent by weight; preservatives, e.g. parabene in an amount of from 0.01 to 1.0 percent by weight; buffer substances, such as sodium citrate or sodium phosphate, in an amount of from 0.1 to 1.0 percent by weight; care substances, e.g. plant and vegetable extracts, proteins and silk hydrolyzates, lanolin derivatives, in an amount of from 0.1 to 5 percent by weight; physiologically compatible silicone derivatives, e.g. volatile or non-volatile silicone oils or high molecular weight siloxane polymers, in an amount of 0.05 to 20 percent by weight; light-protective agents; antioxidants, radical-trapping agents; anti-flaking agents, in an amount of about 0.01 to 2 percent by weight, direct dye compounds, luster-imparting substances, vitamins, softeners and de-fatting agents.

The following example illustrates the invention in more detail, but these details should not be considered as limiting the claims appended hereinbelow.

EXAMPLES

Rasta Hairstyle Setup

The hair is washed with a conventional shampoo, preferably a non-conditioning neutral shampoo. About 6 to 15 g (according to hair length) of the following composition A1 is uniformly distributed on the hair.

Composition A1 (Aerosol Foam):

| | |
|---|---|
| 1 g | Fluisil ® 300 (Silica) |
| 0.8 g | Rewoteric ® AM CAS (Cocamidopropyl hydroxysultaine, 50 percent in water) |
| 0.4 g | Oramix ® NS 10 (Decyl glucoside, 55 percent in water) |
| to 100 g | water |

Composition A1 is filled into an aerosol can with a foam head together with propane/butane in a ratio of 96:4.

Alternatively a hair spray with composition A2 can be sprayed on the dried hair to be intertwined.

Composition A2:

| | |
|---|---|
| 2 g | Fluisil ® 300 (Silica) |
| to 100 g | ethanol. |

The composition A2 is filled into an aerosol can with a spray head with propane/butane (4.8 bar) in a ratio of 96:4.

After drying the hair a crest is pulled, preferably in the shape of a zig-zag crest, and the hairs on the nape of the neck are divided into equal width portions. These portions are subdivided into uniform sized large parts. These large parts are divided into equal sized squares or triangles. To set up an only partial rasta hair style only individual parts of the hair are treated with composition A1 or A2. The hair strands are back-combed gently from the roots to the tips with a gentle twisting motion. The strands are held in the desired fall direction of the dreadlocks during working. After back-combing all the strands of the entire head are sprayed individually with one of the following compositions $B_1$ to $B_5$ and twisted or rotated into the desired shape.

Composition B1:

| | |
|---|---|
| 17.8 g | PEG-60 hydrogenated castor oil |
| 11.9 g | Carnauba wax |
| 8.9 g | PEG-40 hydrogenated castor oil |
| to 100 g | water |

This composition is provided in a container with a pump spray apparatus.

Composition B2:

| | |
|---|---|
| 7.8 g | PEG-60 hydrogenated castor oil |
| 11.9 g | Carnauba wax |
| 9.9 g | PEG-40 hydrogenated castor oil |
| 10 g | Oleth-20 |
| to 100 g | water |

Composition B3 (Aerosol Foam):

| | |
|---|---|
| 20 g | PEG-60 hydrogenated castor oil |
| 10 g | Carnauba wax |
| 2.5 g | Glycerol (86%) |
| 2.5 g | Caprylic/capric triglyceride |
| 35 g | Water |
| to 100 g | Ethanol |

The composition B3 is filled into an aerosol can with a foam head with propane/butane (4.8 bar) in a ratio of 96:4.

Composition B4 (Microemulsion Gel):

First a microemulsion is made from the following composition

| | |
|---|---|
| 10 g | Oleth-10 |
| 9 g | PEG-40 Hydrogenated Castor Oil |
| 10 g | Sucrose Cocoate (92.5%) |
| 10 g | Oleth-5 |
| 12 g | Caprylic/Capric Triglyceride |
| to 100 g | water |

The gel is made according to the following

| | |
|---|---|
| 40 g | Microemulsion |
| 10 g | Acrylates/t-butylacrylamide copolymer (Ultrahold ® 8) |
| 1 g | 2-aminobutanol |
| to 100 g | |

Composition B5 (Gel Wax):

| | |
|---|---|
| 94.5 g | Composition B1 |
| 5 g | Acrylates/t-butylacrylamide copolymer (Ultrahold ® 8) |
| 0.5 g | 2-aminobutanol |
| 11.9 g | Carnauba wax |
| to 100 g | |

Washing of the Rasta Hairstyle

The hairstyle is sufficiently moistened with a shower or gentle water jet under the shower. A mild shampoo is applied to the concave inner side of a concave moistened wash sponge. By dabbing the hair-do (no circular motions) foam is produced from the shampoo. However it is rinsed away gently. After the washing the dreadlocks are again twisted or rotated using one of the compositions B1 to B5.

Removal of the Rasta Hairstyle

After washing a cationic hair care composition of the following composition C is worked into the moist hair.

Composition C:

| | |
|---|---|
| 6.0 g | Cetearyl alcohol |
| 1.35 g | Vaseline ® |
| 1.2 g | Paraffinum Perliquidum |
| 1.0 g | Cetyltrimethyl ammonium chloride |
| 0.3 g | Lanolin alcohol |
| 0.15 g | Lanolin |
| 0.5 g | Silicone oil |
| 0.5 g | Citric acid |
| to 100 g | water |

After an acting time of about five minutes, the dreadlocks are released or removed. The hair care composition then remains on the hair. The dreadlocks are cautiously combed out from the hair tips to the hair roots with a hand comb. After removing the dreadlocks the hair care composition is rinsed out of the hair. Subsequently a desired new hairstyle can be set up.

The disclosure in German Patent Application 102 34 804.9 of Jul. 31, 2002 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a method for setting up, caring for and removing a temporary rasta hairstyle, to compositions and ingredients used in the method and to a multi-part kit for performing the method, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of setting up a temporary rasta hairstyle, said method comprising the steps of:
    (a) applying to the hair at least one roughening composition or at least one composition for making back-combing of the hair easier;
    (b) applying at least one adherence-increasing substance to hair tips and/or the hair; and
    (c) after the applying of step a), intertwining the hair strand-wise to form temporary dreadlocks in order to set up the temporary rasta hairstyle without essentially or irreversibly interlocking the hairs by:
    separating the hair into individual dreadlocks;
    twisting each individual dreadlock over its long axis;
    after 2 to 3 twists, dividing the individual dreadlock at the tips into two divided dreadlocks;
    separating the divided dreadlocks from each other to move the two or three twists toward the hair roots thereby intertwining the individual dreadlock; and repeating the twisting, dividing, and spreading of dreadlocks until the entire length of each individual dreadlock is intertwined.

2. The method as defined in claim 1, wherein said at least one adherence-increasing substance is selected from a group consisting of waxes and adhesive polymer compounds.

3. The method as defined in claim 1, wherein:
    said at least one roughening substance is in the form of solid particles that adhere to the hair,
    the at least one roughening substance is applied to the hair by means of a first composition (A1, A2), and
    said first composition (A1, A2) contains said solid particles in undissolved form, or in dissolved form and the solid particles are precipitated on the hair from said first composition.

4. The method as defined in claim 3, wherein said first composition (A1, A2) contains at least one material selected from a group consisting of silica, silicates, aluminates, clays, mica, salts, metal oxides, minerals, and polymers.

5. The method as defined in claim 4, wherein:
    said first composition (A1, A2) is foamable and contains said silica, at least one foam-forming emulsifier and water and
    said first composition (A1, A2) either contains at least one aerosol propellant or is contained in a container with a mechanical apparatus for producing a foam from the first composition (A1, A2).

6. A method of setting up a temporary rasta hairstyle, said method comprising the steps of:
    (a) applying to the hair at least one roughening composition or at least one composition for making back-combing of the hair easier;
    (b) applying at least one adherence-increasing substance to hair tips and/or the hair; and
    (c) after the applying of step a), intertwining the hair strand-wise to form temporary dreadlocks in order to set up the temporary rasta hairstyle without essentially or irreversibly interlocking the hairs by:
    separating the hair into individual dreadlocks;
    twisting each individual dreadlock over its entire long axis to form a twisted dreadlock;
    holding the tip of the twisted dreadlock fixed and back-combing the hair without interlocking the hairs over the entire axial length of the twisted dreadlock; and
    dividing the twisted dreadlock at the tip into two divided dreadlocks;
    separating the divided dreadlocks from each other to move two or three twists toward the hair roots thereby intertwining the individual dreadlock; and
    rolling the twisted and back-combed dreadlock.

7. The method as defined in claim 6, wherein said at least one adherence-increasing substance is selected from a group consisting of waxes and adhesive polymer compounds.

8. The method as defined in claim 6, wherein said at least one roughening substance is in the form of solid particles that adhere to the hair, the at least one roughening substance is applied to the hair by means of a first composition (A1, A2) and said first composition (A1, A2) contains said solid particles in undissolved form, or in dissolved form and the solid particles are precipitated on the hair from said first composition.

9. The method as defined in claim 8, wherein said first composition (A1, A2) contains at least one material selected from a group consisting of silica, silicates, aluminates, clays, mica, salts, metal oxides, minerals, and polymers.

10. The method as defined in claim 9, wherein said first composition (A1, A2) is foamable and contains said silica, at least one foam-forming emulsifier and water and said first composition (A1, A2) either contains at least one aerosol propellant or is contained in a container with a mechanical apparatus for producing a foam from the first composition (A1, A2).

* * * * *